United States Patent [19]
Asada et al.

[11] 4,277,622
[45] Jul. 7, 1981

[54] PROCESS FOR PRODUCTION OF 1,17-DIAMINO-9-AZAHEPTADECANE

[75] Inventors: Touru Asada; Yasuhisa Miura, both of Hazaki; Tsutomu Yoshino, Yachiyo, all of Japan

[73] Assignee: Dainippon Ink & Chemicals Inc., Tokyo, Japan

[21] Appl. No.: 106,735

[22] Filed: Dec. 26, 1979

[30] Foreign Application Priority Data

Jan. 6, 1979 [JP] Japan .................................. 54-112

[51] Int. Cl.³ ............................................ C07C 85/00
[52] U.S. Cl. .................................... 564/512; 564/498
[58] Field of Search ...................................... 260/583 P

[56] References Cited

U.S. PATENT DOCUMENTS

T945,004  4/1976  Valaitis et al. ............... 260/583 P X
3,217,028  11/1965  Vertnik ........................ 260/583 P X

*Primary Examiner*—John Doll
*Attorney, Agent, or Firm*—Sherman & Shalloway

[57] ABSTRACT

A process for producing 1,17-diamino-9-azaheptadecane, which comprises adding nitric acid, hydrochloric acid, p-toluenesulfonic acid or sulfanilic acid to octamethylenediamine, and heating the mixture to eliminate ammonia therefrom.

5 Claims, No Drawings

PROCESS FOR PRODUCTION OF 1,17-DIAMINO-9-AZAHEPTADECANE

This invention relates to a process for producing 1,17-diamino-9-azaheptadecane of the formula $$H_2N(CH_2)_8NH(CH_2)_8NH_2 \quad (I)$$

which is useful as an intermediate for the synthesis of agricultural chemicals.

The compound of formula (I) is obtained, for example, as a by-product during the production of octamethylenediamine (III) by the hydrogenation of suberonitrile (II) in the presence of a metallic catalyst as schematically shown below, but its yield is very low.

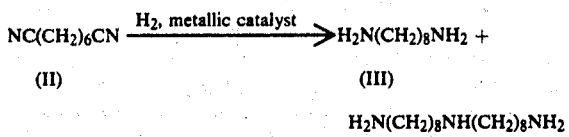

The compound (I) is also obtained by[1] reacting octamethylenediamine in an organic solvent in the presence of a nickel catalyst such as Raney nickel to eliminate ammonia from it. This method has various disadvantages both in regard to economy and safety. Specifically, the reaction requires a large amount of a nickel catalyst (one-half of the weight of the octamethylenediamine). Moreover, since the activity of the catalyst is markedly reduced after one reaction, it cannot be repeatedly used. It is also necessary to purify the solvent used in this process to a high extent so as to remove catalyst poisoning components. Moreover, the reaction should be carried out in an atmosphere of hydrogen, and a large amount of the nickel catalyst must be separated from the organic solvent.

When according to the present invention, octamethylenediamine is heated together with nitric acid, hydrochloric acid (which may be gaseous hydrogen chloride), p-toluenesulfonic acid or sulfanilic acid (to be referred to simply as an "acid") to remove ammonia from it, the compound (I), which is a dimer of the diamine, can be obtained at low cost in a high yield by a simple and safe operation.

In the process of this invention, the amount of the acid used is usually 0.1 to 1.0 equivalent, preferably 0.25 to 0.75 equivalent, per equivalent of octamethylenediamine. When the acid is used in the preferred amounts, the reaction time can be further shortened. Moreover, since the selectivity of the reaction is superior, the ratio of high-boiling trimer or higher polymers to the dimer (compound (I)) can be maintained low. The acids can be used either singly or in combination with each other.

The acid can be added to octamethylenediamine by various methods, for example, a method comprising directly mixing a predetermined amount of the acid with octamethylenediamine; a method comprising melting octamethylenediamine or dissolving it in a suitable solvent, and then adding a predetermined amount of the acid to the molten or dissolved octamethylenediamine; or a method comprising forming a salt between octamethylenediamine and the acid, and adding octamethylenediamine to the salt until the amount of the acid reaches a predetermined value. In the preparation of the octamethylenediamine solution, any solvent which does not participate in the reaction, such as water, alcohols and aromatic solvents, can be used.

The reaction temperature is in the range of generally 150° to 300° C., preferably 180° to 250° C. The selectivity of the reaction is superior within the preferred reaction temperature range.

The ratio of high-boiling trimer and higher polymers of octamethylenediamine to its dimer [compound (I)] tends to increase with higher conversion of the reaction under the same reaction conditions. Thus, to produce the compound (I), it is desirable from an economic viewpoint to stop the reaction when the conversion reaches 10 to 40%, and to recover the starting materials for repeated use.

The deammoniation reaction in accordance with this invention can be performed in the absence of solvent because the starting octamethylenediamine acts as a solvent at the reaction temperature. The reaction can be performed at atmospheric or elevated pressure. Because the ammonia generated comes out of the reaction system without reaction with the acid, the state of the reaction can be traced quantitatively. Scarcely any variation with time in the rate of reaction occurs at the same reaction temperature. Hence, the present invention also has the advantage that the conversion of octamethylenediamine can be controlled as desired.

The following Examples illustrate the process of this invention without any intention of limiting the invention thereby.

EXAMPLE 1

A 500 ml. four-necked flask was charged with 100 g (0.693 mole) of octamethylenediamine and 71.6 g (0.693 mole) of 61% nitric acid, and a thermometer, a stirrer, a distillation device and a nitrogen gas inlet were fitted to the flask. The mixture was heated to 160° C. in a stream of nitrogen, and water within the flask was distilled off. Then, the distillation device was replaced by a reflux condenser, and the reaction was performed while maintaining the inside of the flask at 200° to 205° C. The ammonia generated was conducted to distilled water placed in a beaker from the top of the reflux condenser. By titrating it with a pH indicator and 2 N hydrochloric acid, the state of the proceeding of the reaction was observed.

In 5 hours when the amount of ammonia formed was 0.098 mole, the reaction mixture was cooled to 80° C. Then, 166.5 g of a 20% aqueous solution of sodium hydroxide was added, and the free amine and the inorganic matter were separated. The residue was distilled under reduced pressure. At 110° to 125° C./10 mmHg, 70.1 g of octamethylenediamine was obtained, and at 190° to 220° C./4 mmHg, 23.1 g of the compound (I) was obtained. As distillation bottoms, 4.1 g of high-boiling compounds were obtained. The yield of the compound (I) based on the consumed octamethylenediamine was 82.1%. (In the following, the yield denotes the yield of the compound (I) based on the consumed octamethylenediamine.)

EXAMPLE 2

In the same way as in Example 1, 100 g (0.693 mol) of octamethylenediamine and 35.8 g (0.347 mole) of 61% nitric acid were reacted at 200° to 205° C. for 11 hours. When 0.098 mole of ammonia was generated, the reaction mixture was cooled, and 83.8 g of a 20% aqueous solution of sodium hydroxide was added to separate the amine. The residue was distilled under reduced pressure. Thus, 70.8 g of octamethylenediamine, 22.2 g of the compound (I), and 4.4 g of high-boiling compounds were obtained. The yield of the compound (I) was 80.8%.

EXAMPLE 3

In the same way as in Example 1, 100 g (0.693 mole) of octamethylenediamine and 107.4 g (1.040 moles) of 61% nitric acid were reacted at 200° to 205° C. for 5 hours. When 0.093 mole of ammonia was generated, the reaction mixture was cooled, and 249.5 g of a 20% aqueous solution of sodium hydroxide was added to separate the amine. The residue was distilled under reduced pressure. Thus, 66.8 g of octamethylenediamine, 22.1 g of the compound (I) and 4.7 g of high-boiling compounds were obtained. The yield of the compound (I) was 70.7%.

EXAMPLE 4

In the same way as in Example 1, 100 g (0.693 mole) of octamethylenediamine and 71.6 g (0.693 mole) of 61% nitric acid were reacted at 200° to 205° C. for 3 hours. When 0.052 mole of ammonia was generated, the reaction mixture was cooled, and 166.5 g of a 20% aqueous solution of sodium hydroxide was added to separate the amine. The residue was distilled under reduced pressure. Thus, 83.4 g of octamethylenediamine, 13.4 g of the compound (I) and 1.2 g of high-boiling compounds were obtained. The yield of the compound (I) was 85.8%.

EXAMPLE 5

In the same way as in Example 1, 100 g (0.693 mole) of octamethylenediamine and 70.2 g (0.693 mole) of 36% hydrochloric acid were reacted at 213° to 215° C. for 5 hours. When 0.097 mole of ammonia was generated, the reaction mixture was cooled, and 166.5 g of a 20% aqueous solution of sodium hydroxide was added to separate the amine. The residue was distilled under reduced pressure. Thus, 71.6 g of octamethylenediamine, 21.3 g of the compound (I) and 4.4 g of high-boiling compounds were obtained. The yield of the compound (I) was 79.7%.

EXAMPLE 6

In the same way as in Example 1, 100 g (0.693 mole) of octamethylenediamine and 199.3 g (0.693 mole) of p-toluenesulfonic acid were reacted at 200° to 205° C. for 10 hours. When 0.100 mole of ammonia was generated, the reaction mixture was cooled, and 166.5 g of a 20% aqueous solution of sodium hydroxide was added to separate the amine. The residue was distilled under reduced pressure. Thus, 70.2 g of octamethylenediamine, 22.3 g of the compound (I), and 4.1 g of high-boiling compounds were obtained. The yield of the compound (I) was 79.5%.

EXAMPLE 7

In the same way as in Example 1, 100 g (0.693 mole) of octamethylenediamine and 120 g (0.693 mole) of sulfanilic acid were reacted at 215° to 220° C. for 5 hours. When 0.088 mole of ammonia was generated, the reaction mixture was cooled, and 166.5 g of a 20% aqueous solution of sodium hydroxide was added to separate the amine. The residue was distilled under reduced pressure. Thus, 72.3 g of octamethylenediamine, 20.3 g of the compound (I) and 4.3 g of high-boiling compounds were obtained. The yield of the compound (I) was 77.9%.

What we claim is:

1. A process for producing 1,17-diamino-9-azaheptadecane which comprises adding nitric acid to octamethylenediamine, heating the mixture to eliminate ammonia therefrom, stopping the reaction when the conversion reaches 10 to 40%, and neutralizing the reaction product with an alkali.

2. The process of claim 1 wherein the amount of the acid is 0.1 to 1.0 equivalent per equivalent of octamethylenediamine.

3. The process of claim 1 wherein the amount of the acid is 0.25 to 0.75 equivalent per equivalent of octamethylenediamine.

4. The process of claim 1 wherein the heating is carried out at a temperature of 150° to 300° C.

5. The process of claim 1 wherein the heating is carried out at a temperature of 180° to 250° C.